United States Patent
Younes

(10) Patent No.: US 6,837,242 B2
(45) Date of Patent: Jan. 4, 2005

(54) METHOD AND APPARATUS FOR DETERMINING RESPIRATORY SYSTEM RESISTANCE DURING ASSISTED VENTILATION

(75) Inventor: Magdy Younes, Winnipeg (CA)

(73) Assignee: The University of Manitoba, Winnipeg (CA)

( * ) Notice: Subject to any disclaimer, the term of this patent is extended or adjusted under 35 U.S.C. 154(b) by 0 days.

(21) Appl. No.: 10/258,348

(22) PCT Filed: Apr. 25, 2001

(86) PCT No.: PCT/CA01/00578

§ 371 (c)(1),
(2), (4) Date: Feb. 24, 2003

(87) PCT Pub. No.: WO01/83014

PCT Pub. Date: Nov. 8, 2001

(65) Prior Publication Data

US 2003/0159695 A1 Aug. 28, 2003

Related U.S. Application Data

(60) Provisional application No. 60/199,824, filed on Apr. 26, 2000.

(51) Int. Cl.$^7$ .......................... A61M 16/00; A62B 7/00; F16K 31/02
(52) U.S. Cl. ........................ 128/204.22; 128/204.18; 128/204.21; 128/204.23; 128/204.26
(58) Field of Search ................ 128/204.18, 204.21, 128/204.22, 204.23, 204.26

(56) References Cited

U.S. PATENT DOCUMENTS

| | | | |
|---|---|---|---|
| 4,448,192 A | 5/1984 | Stawitcke | |
| 5,107,830 A | 4/1992 | Younes | |
| 5,129,390 A * | 7/1992 | Chopin et al. | 128/204.21 |
| 5,572,993 A * | 11/1996 | Kurome et al. | 128/204.23 |
| 5,884,622 A | 3/1999 | Younes | |
| 5,931,159 A * | 8/1999 | Suzuki et al. | 128/204.18 |
| 6,158,432 A * | 12/2000 | Biondi et al. | 128/204.21 |
| 6,257,234 B1 * | 7/2001 | Sun | 128/204.18 |
| 6,463,930 B2 * | 10/2002 | Biondi et al. | 128/204.21 |
| 6,526,974 B1 * | 3/2003 | Brydon et al. | 128/205.24 |
| 6,578,575 B1 * | 6/2003 | Jonson | 128/204.21 |

FOREIGN PATENT DOCUMENTS

| | | |
|---|---|---|
| GB | 2077444 | 12/1981 |
| WO | WO 92/11054 | 7/1992 |
| WO | WO 97/22377 | 6/1997 |

* cited by examiner

*Primary Examiner*—Glenn K. Dawson
*Assistant Examiner*—Michael Mendoza
(74) *Attorney, Agent, or Firm*—Sim & McBurney

(57) ABSTRACT

Method and apparatus are described for determining respiratory system resistance (R) in a patient receiving gas from a ventilator. A negative pulse in the pressure and/or flow output of the ventilator during selected inflation cycles is generated and Paw, $\dot{V}$ and V are measured at a point ($T_o$) near the beginning of the pulse, at a point ($T_1$) near the trough of the negative pulse and at a point ($T_{-1}$) preceding $T_o$. The value of R is calculated from the difference between Paw, $\dot{V}$ and V at $T_o$ and at $T_1$ and where the change in patient generated pressure (Pmus) in the interval $T_o$–$T_1$ is estimated by extrapolation from the different between Paw, $\dot{V}$ and V and $T_o$ and at $T_{-1}$, in accordance with Equation 8.

47 Claims, 3 Drawing Sheets

D = Differentiator; EV = Exhalation Valve; P = Potentiometer; $P_{out}$ = Airway Pressure Signal;
V = Volume Signal; $\dot{V}$ = Flow Signal; $\dot{V}_{out}$ = Flow Signal Output Port

METHOD AND APPARATUS FOR DETERMINING RESPIRATORY SYSTEM RESISTANCE DURING ASSISTED VENTILATION

REFERENCE TO RELATION APPLICATIONS

This application is a U.S. National Phase filing under 35 USC 371 of PCT/CA01/00578 filed Apr. 25, 2001 claiming priority under 35 USC 119(e) from U.S. Provisional Patent Application No. 60/199,824 filed Apr. 26, 2000.

FIELD OF INVENTION

This invention relates to mechanical ventilation, and in particular, to assisted ventilation and the determination of respiratory system resistance.

BACKGROUND TO THE INVENTION

There are currently no reliable, clinically available, non-invasive means to estimate respiratory resistance (R) during inspiration in mechanically ventilated patients who have spontaneous respiratory efforts. Calculation of resistance requires knowledge of the force applied to the respiratory system which, in such patients, includes a component related to pressure generated by respiratory muscles (Pmus). This component continuously changes during the inflation phase and cannot be estimated without prior knowledge of respiratory mechanics. Furthermore, to isolate the component of total applied pressure that is dissipated against resistance ($P_{res}$), it is necessary to subtract the pressure used against the elastic recoil of the respiratory system. This requires knowledge of passive respiratory elastance (E) which is also difficult to determine in the presence of unquantifiable Pmus. At present, therefore, R can be reliably estimated only by use of esophageal catheters, which add another invasive intervention to already much instrumented patients, or by elimination of respiratory muscle pressure output with paralysis, or hyperventilation (controlled mechanical ventilation, CMV). The latter entails additional personnel time and does not lend itself to frequent determination of R. To the extent that R is a highly dynamic property that may change frequently, due to secretions or changes in bronchomotor tone, availability of continuous estimates of R may be helpful in the clinical management of such patients. Thus, changes in R can be rapidly identified and dealt with. Furthermore, this information makes it possible to adjust the level of assist according to the prevailing R values, a feature that is of particular utility in pressure assisted modalities of ventilatory support (Pressure Support Ventilation, Proportional Assist Ventilation).

In U.S. Pat. No. 5,884,622 (Younes), assigned to the assignee hereof, an approach is described to determine resistance under similar conditions, namely in assisted ventilation. This prior approach consists of applying at least two different types of transient changes in flow in the course of the inflation phase of the ventilator. The changes in airway pressure (Paw), flow ($\dot{V}$), and volume (V) during these transient flow changes are compared with the time course of these variables in unperturbed breaths. While this approach is capable of providing accurate information about R, it has several limitations. First, because of considerable breath-by-breath variability in the time course of Paw, $\dot{V}$ and V in spontaneous unperturbed breaths, it is necessary to average large numbers of perturbed and unperturbed breaths in order to arrive at the real change that occurred during the perturbation. Accordingly, information about resistance is delayed until a sufficiently large number of observations has been averaged. Furthermore, for the same reasons, any true change in patient's resistance is not detected in a timely way. Second, this approach requires at least two different kinds of perturbations. Because, as indicated earlier, a large number of observations is required with each perturbation, this requirement delays the acquisition of reliable information further. Third, the need to average large numbers of breaths and a large number of data points from each breath, greatly increases the computing and storage requirements of the computer used to process the information to provide the value of R. This requirement adds further strain on the extensive and highly complex operations carried out by modern, computer controlled ventilators.

SUMMARY OF INVENTION

The method and apparatus described in detail herein in accordance with the present invention, represent a considerable simplification of the approach proposed by Younes in U.S. Pat. No. 5,884,622. As indicated above, the main obstacle to determining respiratory resistance during assisted ventilation is the uncertainty about what happens to Pmus during interventions in the course of the inflation phase of the ventilator. The comparison between perturbed and unperturbed breaths was the approach used in U.S. Pat. No. 5,884,622. By contrast, in accordance with the present invention, the behavior of Pmus during the intervention is predicted from estimates of the change in Pmus in the interval immediately preceding the intervention. In this manner, all the required information necessary to determine R can be obtained from a single intervention in a single breath. This approach greatly reduces the computational requirements necessary to determine R, and the time required to obtain information that is clinically useful, such as in assisted ventilation In accordance with the present invention, respiratory resistance (R) is determined while allowing for the presence of pressure generated by respiratory muscles (Pmus) but without requiring knowledge of its actual value or an accurate value of passive respiratory elastance (E).

In accordance with one aspect of the present invention, there is provided a method of determining respiratory system resistance (R) in a patient receiving gas from a ventilatory assist device (ventilator), comprising estimating the flow rate ($\dot{V}$) and volume (V) of gas received by the patient from the ventilator, estimating pressure near the airway of the patient (Paw), generating a signal that results in a step decrease (negative pulse) in the pressure and/or flow output of the ventilator during selected inflation cycles, measuring Paw, $\dot{V}$ and V at a point ($T_O$) near the beginning of the pulse ($Paw_O$, $\dot{V}_O$, $V_O$), at a point ($T_1$) near the trough of the negative pulse ($Paw_I$, $\dot{V}_I$, $V_I$), and at a point ($T_{-1}$) preceding $T_O$ but after the onset of inspiratory effort ($Paw_{-1}$, $\dot{V}_{-1}$, $V_{-1}$); and calculating the value of resistance (R) from the differences between Paw, $\dot{V}$ and V at $T_O$ and at $T_I$ and where the change in patient generated pressure (Pmus) in the interval $T_O \rightarrow T_I$ ($\Delta Pmus(T_O \rightarrow T_I)$) is estimated by extrapolation, from the differences between Paw, $\dot{V}$ and V at $T_O$ and at $T_{-1}$, in accordance with equation (8).

As described in more detail below, the present invention includes modifications to the method as alternative steps to determining R.

In accordance with another aspect of the present invention, there is provided an apparatus which interfaces with ventilatory assist devices (ventilators) determining respiratory system resistance (R), comprising a flowmeter, with associated electronic circuitry, that estimates the flow rate ($\dot{V}$) and volume (V) of gas received by a patient, a pressure sensor that estimates pressure near the airway of the patient (Paw), and electronic circuitry which receives the Paw, $\dot{V}$ and V signals from above mentioned circuitry and which is also connected to the control system of the ventilator, comprising:

circuitry that generates an output that results in a step decrease (negative pulse) in the pressure and/or flow output of the ventilator during selected inflation cycles;

circuitry that measures Paw, $\dot{V}$ and V at a point ($T_O$) near the beginning of the pulse ($Paw_O$, $\dot{V}_O$, $V_O$), at a point ($T_1$) near the trough of the negative pulse ($Paw_1$, $\dot{V}_1$, $V_1$), and at a point ($T_{-1}$) preceding $T_O$ but after the onset of inspiratory effort ($Paw_{-1}$, $\dot{V}_{-1}$, $V_{-1}$);

circuitry to calculate the value of resistance (R) from the differences between Paw, $\dot{V}$ and V at $T_O$ and at $T_I$ and where the change in patient generated pressure (Pmus) in the interval $T_O \rightarrow T_I (\Delta Pmus(T_O \rightarrow T_1))$ is estimated, by extrapolation, from the differences between Paw, $\dot{V}$ and V at $T_O$ and at $T_{-1}$, in accordance with equation (8).

As described in more detail below, the present invention includes modifications to the apparatus as alternative combinations of elements to determine R.

GENERAL DESCRIPTION OF THE INVENTION

According to the equation of motion, the total pressure applied to the respiratory system ($P_{appl}$) is dissipated against elastic, resistive and inertial opposing forces. Thus:

$$P_{appl} = P_{el} + P_{res} + P_{iner}$$

where:

$P_{el}$ is elastic recoil pressure and is given by the product of volume above passive functional residual capacity (FRC) (V) and elastance (E); $P_{el} = V \cdot E$, $P_{res}$ is the pressure dissipated against resistance and is given by the product of flow ($\dot{V}$) and R; $P_{res} = \dot{V} \cdot R$, and, $P_{iner}$ is the pressure dissipated against inertia and is given by the product of flow accelaration (the rate of change in flow in I/sec$^2$; $\ddot{V}$) and inertia (I). Because I of the respiratory system is very small ($\approx 0.02$ cmH$_2$O/l/sec$^2$), $P_{iner}$ can be ignored so long as measurements are made at relatively low $\ddot{V}$ (e.g. <10 I/sec$^2$). In mechanically ventilated patients, $\ddot{V}$ may exceed this level only in the first about 100 to 200 msec of the inflation phase during volume cycled and high level pressure support ventilation (PSV). Accordingly, by avoiding measurements in this region, the equation solved to calculate P can be simplified by neglecting $P_{iner}$.

During assisted ventilation, $P_{appl}$ is made up of two components, one provided by the ventilator (Paw) and one provided by the patient (Pmus). Thus, $P_{appl} = Paw + Pmus$. With this equation and earlier considerations, the equation of motion can be rewritten and rearranged as follows as equation (1):

$$\dot{V} \cdot R = Paw + Pmus - V \cdot E \quad (1)$$

To the extent that Pmus at a given instant is not known, accurate elastance values may not be available and V, relative to passive (FRC), is also not known (in view of possible dynamic hyperinflation or active reduction in volume below FRC by expiratory muscles), it is not possible to solve for R using a set of measurements made at one point during the inflation phase. For this reason, any approach to measure resistance during inflation in such patients must involve measurements at more than one point, having different flow values, as described herein.

Figure 1:
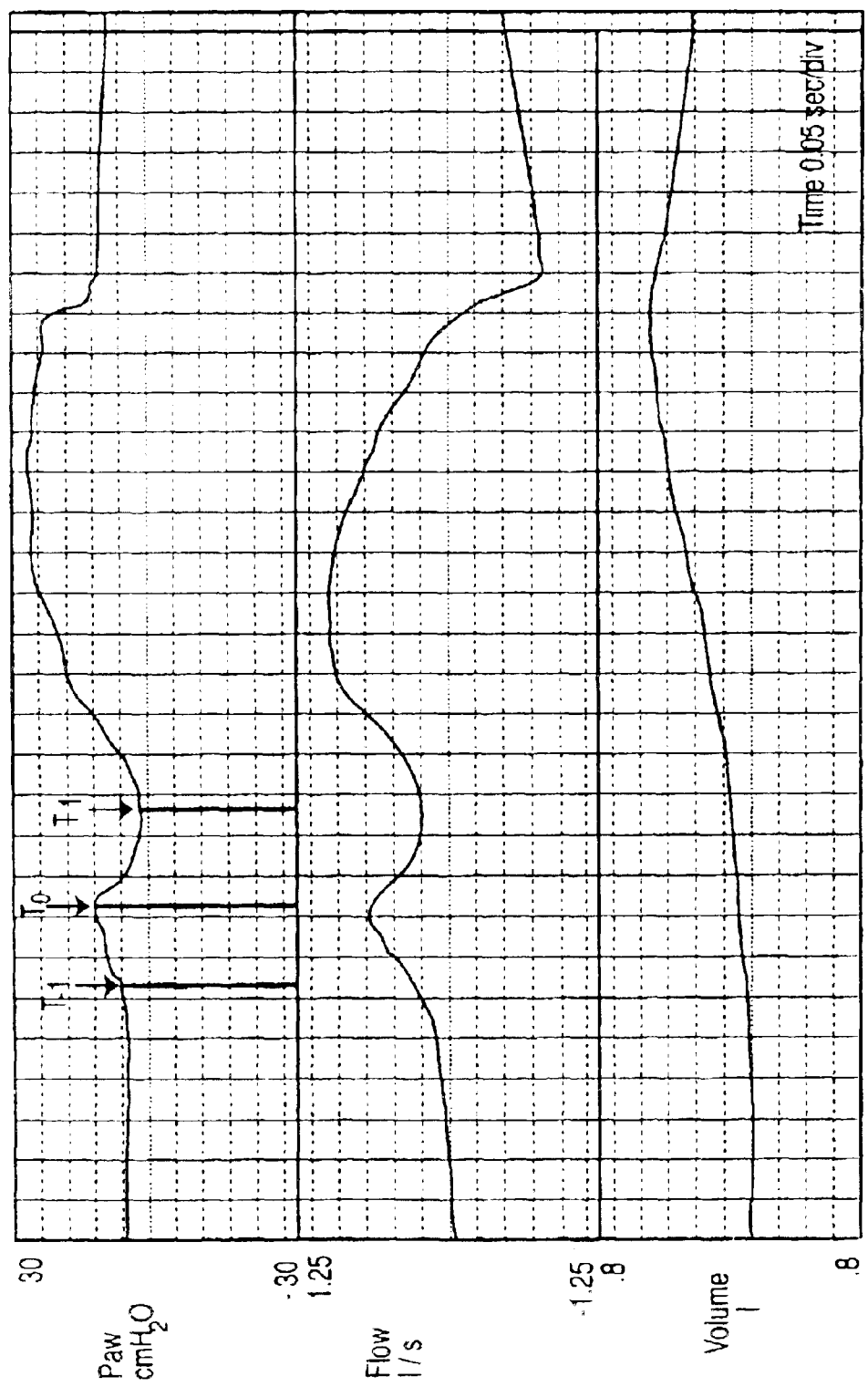
FIG. 1 shows a tracing of airway presence (Paw), flow and volume showing a negative pulse and the three times at which measurements are taken.

In one aspect of the present invention, Paw (and hence flow) is rapidly reduced (negative pulse) during the inflation phase (FIG. 1). Primary measurements of Paw, $\dot{V}$ and V are made at or near the point where Paw and flow begin declining ($T_O$) and at or near the trough of pressure during the negative pulse ($T_I$). These two sampling points are chosen because $\Delta P/\Delta t$ and $\Delta V/\Delta t$ are minimal. In this fashion, inertial forces can continue to be ignored. More importantly, errors related to differences in delay and frequency response of the pressure and flow measuring systems can be avoided. This advantage is particularly relevant since, in modern ventilators, Paw and patient flow are not measured directly near the ET tube but are estimated from remote sites and, hence, the signals may be subject to different delays and response characteristics. Even minor differences in these properties can cause serious errors when Paw and patient flow are changing rapidly (for example, during the declining phase of the pulse).

Equation 1 can be written for $T_O$ and $T_I$ as follows, as equations (2) and (3):

$$\dot{V}_{(O)} \cdot R = Paw_{(O)} + Pmus_{(O)} - V_{(O)} \cdot E \quad (2)$$

$$\dot{V}_{(1)} \cdot R = Paw_{(1)} + Pmus_{(1)} - V_{(1)} \cdot E \quad (3)$$

Subtracting equation 3 from equation 2 yields equation (4):

$$R(\dot{V}_{(O)} - \dot{V}_{(1)}) = (Paw_{(O)} - Paw_{(1)}) + (Pmus_{(O)} - Pmus_{(1)}) - E(V_{(O)} - V_{(1)}) \quad (4)$$

Rearranging equation (4) to solve for R:

$$R = [(Paw_{(O)} - Paw_{(1)}) + \Delta Pmus(T_O \rightarrow T_I) - E(V_{(O)} - V_{(1)})]/(\dot{V}_{(O)} - \dot{V}_{(1)})$$

In theory, if the time interval between $T_O$ and $T_I$ (i.e. $\Delta t$) is infinitely small, the differences in Pmus and in volume can be ignored and $\Delta Paw$ becomes $\Delta Pres$. In practice, however, during mechanical ventilation it is not possible to instantly reduce flow from one value to another relatively stable value (i.e. at which $\Delta P/\Delta t$ and $\Delta \dot{V}/\Delta t$ are acceptably small). Even if flow exiting the ventilator is altered suddenly, a finite time must elapse before the flow to the patient stabilizes at the new value in view of continued flow from the tubing to patient in the process of decompression of the circuit. $\Delta t$, therefore, cannot be made short enough to ignore changes in Pmus between $T_O$ and $T_1$ and $\Delta Pmus$ in this interval has to be accounted for.

In this aspect of the present invention, the change in Pmus between $T_O$ and $T_1$ is estimated by assuming that Pmus changes in this time range at the same rate as in the period immediately preceding $T_O$. This is not an unreasonable assumption if the time interval between $T_O$ and $T_1$ is relatively brief (for example, approximately 100 msec). The rate of change in Pmus immediately before the pulse is estimated by sampling Paw, $\dot{V}$ and V at a point shortly before $T_0$ (for example, 100 msec prior to $T_O$)($T_{-I}$), (FIG. 1). The following two equations (5) and (6) provide estimates of Pmus at $T_O$ and $T_{-1}$ respectively and represent rearrangement of the equation of motion (equation (1)):

$$Pmus_O = V_O \cdot E + \dot{V}_O \cdot R - Paw_O \qquad (5)$$

$$Pmus_{-I} = V_{-I} \cdot E + \dot{V}_{-1} \cdot R - Paw_{-1} \qquad (6)$$

Subtracting equation 6 from equation 5 and dividing by $\Delta t{-1}$ (time between $T_O$ and $T_{-1}$) gives $\Delta Pmus/\Delta t$ in the interval ($\Delta t_1$) prior to $T_O$ according to equation (7):

$$\Delta Pmus/\Delta t = (1/\Delta t_{-I})[E(V_O - V_{-I}) + R(\dot{V}_O - \dot{V}_{-1}) - Paw_O + Paw_{-I}] \qquad (7)$$

Assuming that Pmus changes at the same rate between $T_O$ and $T_I$, the change in Pmus between these two points is given by:

$$(Pmus_O - Pmus_1) = -\Delta t_I \qquad [\text{equation 7}]$$

where $\Delta t_I$ is the time interval between $T_1$ and $T_O$.

Substituting [$-\Delta t$ (equation 7)] for ($Pmus_O - Pmus_1$) in equation 4 and rearranging provides equation (8):

$$R = [(Paw_O - Paw_I + (\Delta t/\Delta t_{-1})(Paw_O - Paw_{-1})) - E(V_O - V_1 + (\Delta t/\Delta t_{-1})(V_O - V_{-1}))]/(\dot{V}_O - \dot{V}_1 + (\Delta t/\Delta t_{-1})(\dot{V}_O - \dot{V}_{-1})) \qquad (8)$$

The only unknown in the numerator of equation 8, which is the estimate of Pres, is E. However, unlike the case in equation 4, the difference in V between $T_O$ and $T_1$ is now reduced by the term ($\Delta t_1/\Delta t_{-1}$)($V_O - V_{-1}$). If the pulse is initiated during the rising phase of flow (e.g. FIG. 1), average $\dot{V}$ in the intervals $T_{-1}$ to $T_O$ and $T_O$ to $T_1$ will not be substantially different and, given that the time intervals between $T_O$ and $T_I$ and between $T_O$ and $T_1$ are quite small (ca 0.1 sec), the entire volume term is reduced to nearly zero. Under these conditions, any errors in estimating E should result in very minor errors in estimating Pres, and hence resistance (R), and, in the absence of a known value of E, a default value, representing, for example, average E in ventilator dependent patients, can be used without much risk of significant errors. It should also be noted that, because all volume points are obtained from the same breath, differences between any two volume values represent differences in absolute volume, relative to passive FRC. As a result, offsets of volume, relative to passive FRC, at the beginning of the breath become irrelevant.

The above derivation of equation 8 entails the assumption that the value of R is constant or, specifically, that R is independent of flow and volume. In reality, R may vary with flow, particularly in intubated patients, if only because the resistance of the endotracheal tube increases with flow. Likewise, R may be dependent on lung volume in some patients. Equation 8 can be adapted to allow for R being flow and/or volume dependent. The number of mathematical functions that can be used to characterize flow or volume dependence of R is infinite. It would be impractical to provide formulations of equation 8 that allow for all conceivable mathematical descriptions of flow and/or volume dependence. Rather, one example will be illustrated which represents the most widely accepted behavior of R in mechanically ventilated intubated patients, namely that R is minimally (or not at all) affected by volume but that it increases with flow according to Rohrer's equation ($R = K_1 + K_2 \dot{V}$). It is recognized, however, that any individual with modest mathematical skills can utilize the same information obtained in this aspect of the present invention (i.e. Paw, V and $\dot{V}$, measured at $T_O$, $T_I$ and at points preceding $T_O$) to derive the pressure-flow relation where mathematical functions other than Rohrer's equation are assumed to apply.

The following equations (2a to 8a) correspond to equations 2 to 8 above after making appropriate modifications to allow for R to increase with flow according to Rohrer's equation ($R = K_1 + K_2 \dot{V}$):

$$K_1 \dot{V}_O + K_2 \dot{V}_O^2 = Paw_O + Pmus_O - V_O \cdot E \qquad (2a)$$

$$K_1 \dot{V}_1 + K_2 \dot{V}_O^2 = Paw_1 + Pmus_1 - V_1 \cdot E \qquad (3a)$$

$$K_1(\dot{V}_O - \dot{V}_I) + K_2(\dot{V}_O^2 - \dot{V}_1^2) = (Paw_O - Paw_1) + (Pmus_O - Pmus_I) - E(V_O - V_1) \qquad (4a)$$

$$Pmus_O = V_O \cdot E + \dot{V}_O \cdot K_1 + V_O^2 \cdot K_2 - Paw_O \qquad (5a)$$

$$Pmus_I = V_{-I} \cdot E + \dot{V}_{-I} \cdot K_1 + V_{-1}^2 \cdot K_2 - Paw_{-1} \qquad (6a)$$

$$\Delta Pmus/\Delta t = (1/\Delta t_{-1})[E(V_O - V_1) + K_1(\dot{V}_O - \dot{V}_{-I}) + K_2(\dot{V}_O^2 - \dot{V}_{-I}^2) - Paw_O + Paw_{-1}] \qquad (7a)$$

$$K_1(\dot{V}_O - \dot{V}_1 + (\Delta t_1/\Delta t_{-1})(\dot{V}_O - \dot{V}_{-1})) + K_2(\dot{V}_O^2 - \dot{V}_I^2 + (\Delta t1/\Delta t - 1)(\dot{V}_{O}^2 - \dot{V}_{O-I}^2)) = (Paw_O - Paw_I + (\Delta t/\Delta t_{-1})(Paw_O - Paw_{-1})) - E(V_O - V_I + (\Delta t/\Delta_{-1})(V_O - V_{-1})) + \text{tm} \qquad (8a)$$

From each applied pulse, an equation of the form of equation (9) accordingly results:

$$K_1 \cdot X + K_2 \cdot Y = Z \qquad (9)$$

where X is the flow term (first bracketed term to left of equation 8a), Y is the $\dot{V}^2$ term (second bracketed term in equation 8) and Z is the Pres term (right side of equation 8). To obtain Z, a known value of E is used or, in the absence of this information, a default value (e.g. 28 cmH$_2$O/l, representing average E in mechanically ventilated patients (personal observations), may be used. Resistance can be obtained from the above equation (9) in one of several ways. Some of these are listed below:

1) $K_2$ is initially assumed to be zero and resistance is estimated from Z/X. The resistance value obtained in this fashion represents the slope of the P $\dot{V}$ relation between $\dot{V}_O$ and weighted average of $\dot{V}_I$ and $\dot{V}_{-I}$. If $\dot{V}_I$ and $\dot{V}_{-1}$ are not substantially different (e.g. FIG. 1), R calculated in this fashion can be assumed to represent the slope of the P $\dot{V}$ relation between $\dot{V}_O$ and either $\dot{V}_1$ or $\dot{V}_{-I}$ or the mathematical average of the two. It can be shown, using Rohrer's equation, that the slope of the P $\dot{V}$ relation between any two flow points (incremental resistance, IR) is the same as the resistance at a flow corresponding to the sum (flow-sum) of the two flow points (in this case ($\dot{V}_O + \dot{V}_1$)). With this treatment, R is reported as resistance at a specific flow (i.e. flow sum).

2) If a range of flow-sum values is obtained in successive pulses, either spontaneously or by design, a range of IR values will also result. A regression between IR (dependent variable) and flow-sum will result in a significant correlation if a sufficiently wide range of flow-sum is present. The intercept of this regression is $K_I$ and the slope is $K_2$. These can be reported as such. Alternatively, resistance may be reported as the sum of $K_I$ and $K_2$, which is resistance at a standard flow of 1.0 l/sec. This has the advantage that changes in reported resistance reflect real changes in resistance whereas with approach #1, alone, the reported resistance may change simply because flow is different.

3) The values of $K_1$ and $K_2$ can be derived from the results of two pulses having different X and Y values, or by regression analysis of the results of multiple pulses displaying a range of X and Y values. The procedure of applying pulses can be deliberately planned to result in a wide range of X and Y values in order to facilitate this analysis. For example, pulses may be initiated at different flow rates, so that $\dot{V}_O$ is variable, and/or the decrease in $\dot{V}$ during the pulse can also be deliberately varied, to result in a range of $\dot{V}_1$.

4) In the absence of reliable, directly determined $K_1$ and $K_2$ values, following approach #2 above, $K_2$ can be assumed to equal $K_2$ of the endotracheal tube (ET) and equation 9 is solved for $K_1$. Thus, $K_1=(Z-(Y \cdot K_2ET))/X$. The $K_2$ values of clean ET tubes of different sizes are widely available. Resistance can be reported as $K_1+K_2ET$, reflecting resistance at a standard flow of 1.0 l/sec. The resistance so reported may differ from actual resistance at 1 l/sec to the extent that actual $K_2ET$ may differ from the assumed $K_2$ of a clean tube AND the flow at which R estimates are made are different from 1.0 l/sec. The error in estimated resistance (at 1 l/sec), if actual $K_2$ ($K_2$ actual) is different from assumed $K_2$ is given by $R_{error}=(K_2 \text{ actual}-K_2 \text{ assumed})(1-Y/X)$. It can be seen that the error in estimating R at 1 l/sec using an assumed $K_2$ is a fraction of the difference between the actual and assumed $K_2$ value.

Potential Sources of Errors and Approaches to Minimize Such Errors:

1) Measurement Noise:

In mechanically ventilated patients, the Paw and $\dot{V}$ signals are subject to noise from multiple sources. These include airway secretions, cardiac artifacts, liquid in the tubing and oscillations or vibrations in the flow delivery system of the ventilator. The noise in the Paw signal may be in phase or out of phase with that in the $\dot{V}$ signal depending on the source of noise and the frequency response of the two measuring systems. Out of phase noise has a greater impact on estimated R particularly if the critical measurements (e.g. at $T_O$, $T_I$ and $T_{-1}$) are obtained from discrete points of unfiltered signals. Such noise results in an increased random variability of estimated R in successive measurements. A more systematic error may result if the pulse is programmed to begin when a certain flow is reached. Here, there is an increased probability that the pulse will begin on the upswing of a positive flow artifact.

Errors related to measurement noise can be reduced by a variety of approaches:

a) The most effective approach is to insure that the change in flow produced by the intervention (i.e. change in flow between $T_O$ and $T_I$) is large relative to the amplitude of the noise.

b) Elimination of sources of noise to the extent possible.

c) Critical filtering of the Paw and $\dot{V}$ signals.

d) To minimize systematic errors, the pulse should preferably not begin when a fixed level of flow is reached (see above).

e) Averaging the resistance results obtained from a number of pulses.

2) Difference in Response Characteristics of Paw and $\dot{V}$ Measuring Systems:

Difference in response characteristics of the measuring systems causes the peak and trough of the measured pressure to occur at different times relative to the flow signal even if the peaks and troughs of the two signals were, in reality, simultaneous. If $T_O$ is taken as the time of peak Paw, flow at $T_O$ will underestimate real flow, and vice versa Also, such differences convert the relatively innocuous in-phase oscillations originating from ventilator flow delivery systems to potentially more serious out-of-phase oscillations in Paw and flow. To minimize the impact of these differences, the phase lag between the Paw and flow measuring systems should be as short as possible over the frequencies of interest. In addition, the pulse can be designed to avoid sharp peaks and troughs.

3) Errors Related to Extrapolation of the Pmus Trajectory:

These are potentially the most serious particularly when respiratory drive, and hence $\Delta Pmus/\Delta t$, is high. The proposed approach involves the assumption that $\Delta Pmus/\Delta t$ during the pulse is the same as $\Delta Pmus/\Delta t$ over a finite period prior to the pulse. This assumption can be in error for a variety of reasons. These, and possible ways to minimize these potential errors, are discussed below:

a) Termination of inspiratory effort (neural $T_i$) during the pulse: This can potentially produce the largest errors in estimated R. Thus, assume that $\Delta Pmus/\Delta t$ prior to $T_O$ is 40 $cmH_2O/sec$ and $\Delta t_I$ (i.e. $T_I-T_O$) is 0.15 sec. The estimated increase in Pmus between $T_O$ and $T_1$ would be 6 $cmH_2O$. If, however, neural $T_i$ ends near $T_O$, Pmus will decrease instead of increasing. Because the rate of decline in Pmus during neural expiration is fastest soon after the end of neural $T_i$, the decrease in Pmus may actually be greater than the assumed extrapolated increase, with the error in estimated $\Delta Pmus$ being >12 $cmH_2O$. It can be seen from equation 4 that this condition translates into an error of corresponding magnitude in estimated Pres. If the difference between $\dot{V}_O$ and $\dot{V}_1$ is 0.4 l/sec, this error would translate into an error of >30 $cmH_2O/l/sec$ in estimated resistance.

Because of the potentially large magnitude of this error, it is necessary to insure that peak Pmus (end of $T_i$) does not occur between $T_O$ and $T_I$. This condition is easy to accomplish during Proportional Assist Ventilation (PAV). In this mode, the end of ventilator cycle is automatically synchronized with patient effort and is constrained to occur during the declining phase of Pmus. So long as pulses are not delivered in the last fraction (ca 30%) of ventilator $T_1$, one is assured that $T_i$ termination did not occur within the pulse. With pressure support ventilation (PSV) and assisted volume-cycled ventilation, such synchrony is not assured, however, and $T_i$ may terminate at any point within or even beyond the inflation phase. $T_i$ termination may occur, per chance, during some of the pulses resulting in errors of differing magnitudes depending on $\Delta Pmus/\Delta t$ prior to the pulse, the point within the pulse at which $T_i$ terminated, the rate of decline in Pmus beyond the peak, and the difference in flow between $T_O$ and $T_1$. Considerable variability may occur between the results of different pulses. For this reason, application of this approach during PSV and volume cycled ventilation may produce less reliable resistance values.

b) Shape of the rising phase of Pmus: The rate of rise of Pmus during the rising phase is not constant. Differences between $\Delta Pmus/\Delta t$ in the interval $T_O$ to $T_I$ (i.e. $\Delta t_1$) and $T_{-I}$ to $T_O$ (i.e. $\Delta t_{-1}$) causes errors in estimated R for the same reasons discussed under (a) above. A $\Delta t$ of approximately 0.1 sec is both feasible and consistent with minimal errors related to response characteristics of the measuring systems. It is unlikely that an important change in $\Delta Pmus/\Delta t$ would occur over this brief time interval, provided all measurement points (i.e. $T_O$, $T_I$, $T_{-I}$) occur during either the rising or declining phase of Pmus. What needs to be avoided is the occurrence of $T_i$ termination between $T_{-I}$ and $T_I$ and this can be accomplished by insuring that pulse application occurs either early in the inflation phase or very late in the inflation phase in the PAV mode. In this mode, there is assurance that pulses applied in the first 50% of the inflation phase occur, in totality (i.e. $T_{-1}$ to $T_1$), on the rising phase of Pmus while pulses applied very near the end of the inflation phase will occur in totality on the declining phase of Pmus. In either case, there is little likelihood of a major change in $\Delta Pmus/\Delta t$ over the brief period of the pulse and extrapolation from one segment to the next, within the brief pulse period, should not result in significant errors.

c) Behavioral responses: The change in Pmus following the initiation of the pulse may deviate dramatically from that expected from the preceding time interval if the patient perceives the pulse and reacts behaviorally to it. The minimum latency for behavioral responses to changes in Paw and flow is approximately 0.2 sec, even in very alert normal subjects. It follows that errors related to perception of the pulse, with consequent behavioral responses, can be avoided if measurements are restricted to the approximately 0.2 sec interval after initiation of the pulse. Behavioral responses, however, can occur without perception if the change is anticipated. For example, if a perturbation occurs regularly every 5 breaths, the patient may alter his/her respiratory output every fifth breath, even before the pulse is initiated. The occurrence of anticipatory responses can be minimized by randomizing the order of pulse applications.

d) Non-behavioral neuromuscular responses to changes in flow: The rapid reduction in flow in the course of an ongoing inspiratory effort may, theoretically, elicit reflex changes in neural output with much shorter latencies than behavioral responses. In addition, the change in flow and, consequently, in time course of volume, may elicit changes in Pmus, independent of changes in electrical activation, through the operation of the intrinsic properties of respiratory muscles (force-length and force-velocity relations). An important contribution from either of these responses following the onset of the pulse (between $T_O$ and $T_f$) could alter the time course of Pmus relative to the course predicted from the pre-pulse interval and introduce errors in estimated Pres. Based on experimental results, these effects are likely to be small if the change in flow is modest (for example, <1 l/sec) and the intervention is carried out early in the inflation phase where Pmus is relatively low.

e) Pmus noise: Noise in the Pmus signal can introduce errors when the change in Pmus over a relatively brief period (for example, 0.1 sec) is used to estimate the change in a subsequent interval. Pmus noise can be real or artifactual. Tracings of $P_{di}$ (transdiaphragmatic pressure), for example, often have a jagged rising phase. Furthermore, when Pmus is estimated from P, $\dot{V}$ and V, as opposed to being measured, independent noise in the pressure and flow signals (for example, cardiac artifact, secretions . . . etc) can introduce noise in estimated Pmus, even if the true rising phase of Pmus is smooth. The impact of Pmus noise on estimated resistance is the same whether the noise is real or artifactual. Random noise in the Pmus signal may be expected to increase variability in measured resistance values, reducing the reliability of information obtained from single pulses. This condition can be dealt with by averaging the results of several observations over a number of breaths. Furthermore, the impact of Pmus noise can also be reduced by using a relatively large change in flow between $T_O$ and $T_1$.

Alternative Approaches to Calculation of Resistance Using the Pulse Technique:

1) Estimation of the change in Pmus during the pulse using an interpolation approach:

In the above description, the change in Pmus between $T_O$ and $T_1$ (i.e. $\Delta Pmus(T_O \rightarrow T_1)$) was estimated by extrapolation of the Pmus trajectory in the interval $T_{-1}$ to $T_O$. An alternative approach is to estimate $\Delta Pmus(T_O \rightarrow T_1)$ by interpolation between two points, one before (for example, at $T_O$) and one after the trough of Paw ($T_2$). In this case, Paw, $\dot{V}$ and V are measured at $T_O$ (i.e. $Paw_O$, $\dot{V}_O$ and $V_O$) and at $T_2$ (i.e. $Paw_2$, $\dot{V}_2$ and $V_2$) in addition to at $T_1$. $T_2$ should preferably be chosen at a point, after $T_1$, where $\Delta Paw/\Delta t$ and/or $\Delta \dot{V}/\Delta t$ are very small to minimize inertial forces. With this alternative approach, equation 8 can be written as follows:

$$R=[(Paw_O-Paw_1+(\Delta t_1/\Delta t_2)(Paw_2-Paw_O))-E(V_O-V_1+(\Delta t_1/\Delta t_2)(V_2-V_O))]/(\dot{V}_O-\dot{V}_1+(\Delta t_1/\Delta t_2)(\dot{V}_2-\dot{V}_O)) \quad \text{(8 inter)}$$

where $\Delta t_2$ is the interval between $T_2$ and $T_O$. Equation 8a can be written as follows:

$$K_1(\dot{V}_O-\dot{V}_1+((\Delta t_1/\Delta t_2)(\dot{V}_2-\dot{V}_O)))+K_2(\dot{V}_O^2-\dot{V}_1^2+((\Delta t_1/\Delta t_2)(\dot{V}_2^2-\dot{V}_O^2)))$$
$$=(Paw_O-Paw_1+((\Delta t_1/\Delta t_2)(Paw_2-Paw_O)))-E(V_O-V_1+((\Delta t_1/\Delta t_2)(V_2-V_O))) \quad \text{(8a inter)}$$

There are advantages and disadvantages to the interpolation approach, relative to the extrapolation approach described earlier. The main advantage is that, in principle, estimating an unknown value by interpolation between values before and after the unknown value is more accurate than estimating the unknown value through extrapolation of data points which are all occurring before or after the unknown value. The practical disadvantages in this particular application, however, are that point $T_2$ occurs beyond the pulse intervention and, as well, later in inspiration. Pmus at $T_2$ may thus be corrupted through behavioral or reflex responses to the preceding intervention, and by the greater likelihood that termination of inspiratory effort with precipitous decrease in Pmus, may occur prior to $T_2$.

2) Combined use of the extrapolation and interpolation techniques:

R can be estimated using both the extrapolation technique (equation 8 or 8a) and the interpolation technique (equation 8 inter and 8a inter) and the results of the two approaches may be averaged using a suitable averaging technique.

While either the interpolation approach or the combined approach may be used in preference to the extrapolation technique, my practical experience favors the extrapolation technique. Thus, it was found in studies on 67 ventilator dependent patients that the results of the extrapolation approach are in closer agreement with results obtained during controlled ventilation than the results of the other two alternative approaches.

3) Use of back extrapolation, instead of forward extrapolation, of Pmus:

The change in Pmus between $T_O$ and $T_1$ can be estimated by back extrapolation of data from a period following $T_1$. Thus, Paw, $\dot{V}$ and V are measured at $T_2$ (see alternative approach #1 above). Equation 8 and 8a are modified to reflect these sampling points as follows:

$$R=[(Paw_O-Paw_1+(\Delta t_f/\Delta t_2)(Paw_2-Paw_1))-E(V_O-V_1+(\Delta t_f/\Delta t_2)(V_2-V_1))]/(\dot{V}_O-\dot{V}_1+(\Delta t_1/\Delta t_2)(\dot{V}_2-\dot{V}_1)) \quad \text{equation 8 (bextra)}$$

and $$K_1(\dot{V}_O-\dot{V}_1+(\Delta t_1/\Delta t_2)(\dot{V}_2-\dot{V}_1))+K_2(\dot{V}_O^2-\dot{V}_1^2+((\Delta t_1/\Delta t_2)(\dot{V}_2^2-\dot{V}_1^2)))$$
$$=(Paw_O-Paw_1+((\Delta t_1/\Delta t_2)(Paw_2-Paw_1)))-E(V_O-V_1+((\Delta t_f/\Delta t_2)(V_2-V_1))) \quad \text{equation 8a (bextra)}$$

4) $\Delta Pmus/\Delta t$ prior to $T_O$ can be estimated from values obtained at two points both of which occurring before $T_O$ (e.g. $T_{-1}$ and $T_{-2}$). Although feasible and should provide reasonably accurate results, it has little advantage over the use of $T_O$ and only one preceding point, while adding more computation complexities.

5) Use of regression analysis to estimate $\Delta Pmus/\Delta t$ prior $T_O$ or beyond $T_1$: The extrapolation approach described above utilizes measurements at only two points (e.g. $T_O$ and $T_{-1}$) to estimate $\Delta Pmus/\Delta t(T_O \rightarrow T_1)$. Although computationally much more intensive, $\Delta Pmus/\Delta t$ prior to the onset of the pulse, or between $T_1$ and $T_2$, can be estimated by sampling Paw, $\dot{V}$ and V at multiple points prior to, or after, the pulse and estimating $\Delta Pmus/\Delta t$ by suitable regression analysis. The standard equations for linear and non-linear regression can be applied to the multiple data sets, to obtain an estimate of Paw, $\dot{V}$ and V at $T_1$. These are then inserted at the appropriate locations in equations 8 and 8a.

6) Use of positive flow pulses (transients): Whereas there is described above the application of the procedure of the invention using negative Paw and flow transients (for example, FIG. 1), the same approach can be applied to imposed positive flow and Paw transients. Here, Paw, $\dot{V}$ and volume are also measured immediately before the perturbation ($T_O$), at or near the point of maximum Paw (or flow) of the positive pulse ($T_1$) (as opposed to the trough of the negative pulse) and at a third point, either before $T_O$, to implement the extrapolation technique, or after $T_1$, to implement the interpolation or back extrapolation techniques. The values of Paw, $\dot{V}$ and V obtained at the three points ($T_O$, $T_1$ and $T_{-1}$ or $T_O$, $T_1$ and $T_2$) are then inserted in equation 8 or 8a (for extrapolation approach), 8 inter or 8a inter (for interpolation approach) or 8 (bextra) and 8a (bextra) (for the back extrapolation approach). Regression analysis can also be used on multiple data prior to $T_O$. In my experience, negative pulses provide more reliable results and are, therefore, preferred. The more reliable result using negative pulse is likely related to two factors. First, negative pulses dictate the occurrence of a point at which $\Delta Paw/\Delta t$ is zero, which can be used as $T_O$ (see FIG. 1). With positive pulses, this cannot be assured. There are advantages to making the measurements at points where $\neq Paw/\Delta t$ and $\Delta \dot{V}/\Delta t$ are near zero, (as discussed above). Second, in many patients there are substantial differences in time of occurrence of peak flow and peak Paw when positive pulses are given, which introduces uncertainty in the results.

DESCRIPTION OF PREFERRED EMBODIMENT

Figure 2:
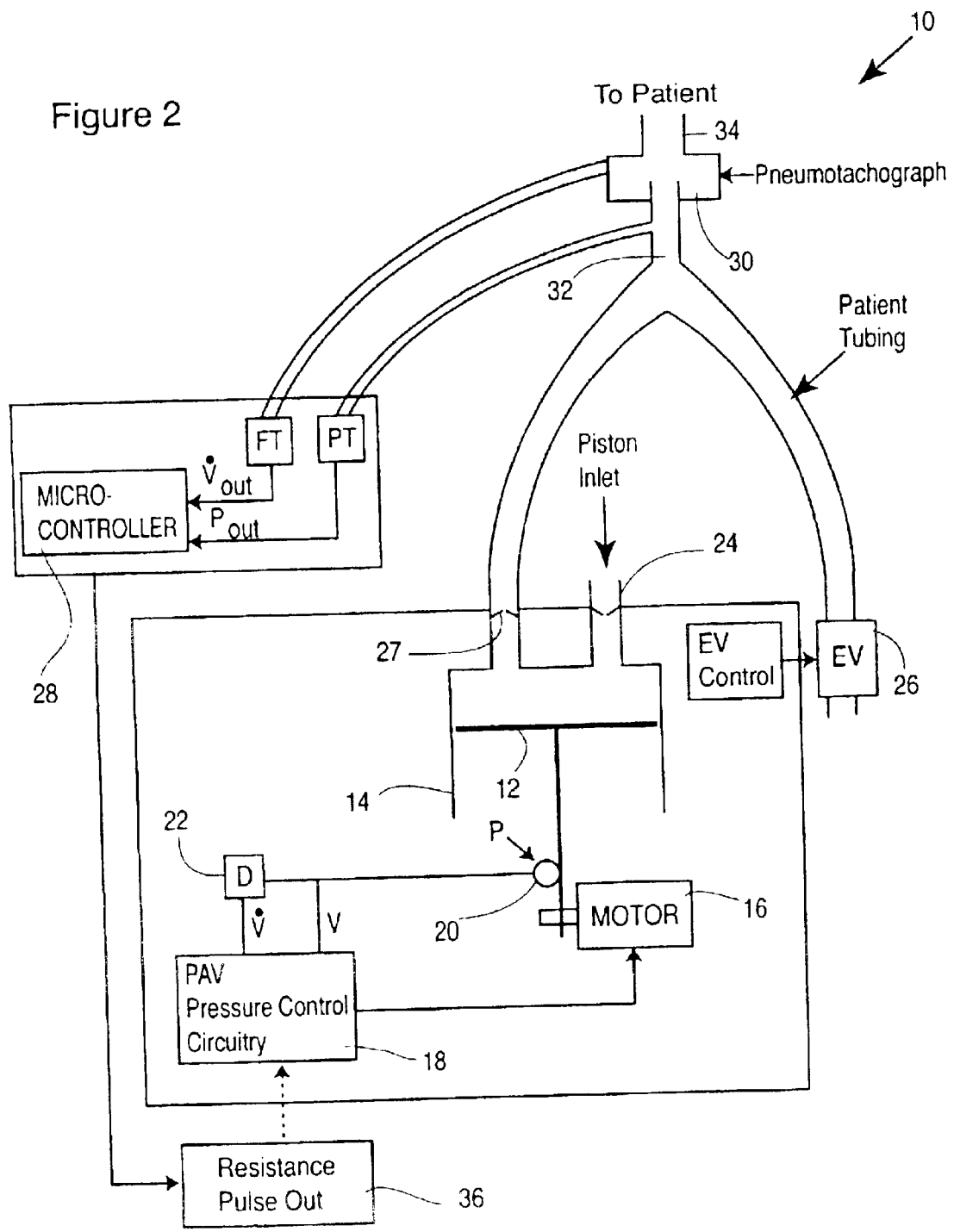
FIG. 2 is a schematic representation of apparatus for carrying out the method in accordance with a preferred embodiment of the invention.

FIG. 2 shows an overview of a preferred embodiment of apparatus for carrying out the present invention. This preferred embodiment reflects the actual system used to validate the inventive procedures of the invention in 67 ventilator-dependent patients. The preferred embodiment has several components. Although in FIG. 2, these components are shown as distinct from each other, such representation is for the sake of illustration of these components, in actual practice all three components can be incorporated within a single unit (the ventilator).

A gas delivery unit 10 is a ventilator system that is capable of delivering proportional assist ventilation (PAV). A variety of mechanical systems can be used to deliver PAV and some are commercially available, which use blower-based, piston-based and proportional solenoid systems. PAV is described in U.S. Pat. No. 5,107,830 (Younes), assigned to the assignee hereof and the disclosure of which is incorporated herein by reference. The ventilator illustrated in the preferred embodiment consists of a piston 12 reciprocating within a chamber 14. The piston 12 is coupled to a motor 16 that applies force to the piston 12 in proportion to input received from the PAV pressure control unit 18. A potentiometer 20 measures the piston displacement which corresponds to the volume change during the ventilator cycle. After certain corrections related to leaks and gas compression, this signal conveys the amount of gas (volume) received by the patient. The volume signal (V) is differentiated using a suitable differentiator 22 to result in a flow signal ($\dot{V}$). The PAV pressure control unit 18 generates a signal that is the sum of a suitably amplified flow signal and a suitably amplified volume signal with amplification factors being set by the user, which signal is used to control the motor 16. The piston chamber 14 receives suitable gas mixture through an inlet port 24 and delivers gas to the patient through an outlet port. During inspiration, an exhalation valve control circuit closes the exhalation valve 26 ensuring that the gas pumped by the piston 12 is delivered to the patient through valve 27. At the end of the inspiratory cycle, the exhalation valve control circuit opens the exhalation valve 26 to allow expiratory flow to occur prior to the next cycle.

A micro controller 28 receives the flow and airway pressure signals. These can be obtained directly from ventilator outputs of flow ($\dot{V}$) out and airway pressure (P). Alternatively, flow and airway pressure are measured independently by inserting a pneumotachograph (30) and an airway pressure outlet between the Y connector 32 and the patient. The latter approach is the one illustrated in FIG. 2. Pressure transducers are provided (FT and PT) to generate signals in proportion to airflow and airway pressure near the endotracheal tube 34. Although this is a more direct way of estimating patient flow and airway pressure, reasonably accurate estimates can be obtained from sensors within the ventilator body, remote from the patient, after allowances are made for tube compression. The patient flow and airway pressure signals are continuously monitored by the micro controller 28. At random intervals, electric pulses are generated by the micro controller and are conveyed to the PAV delivery system via suitable output ports. These pulses may be either negative or positive, as described above. The pulse output is connected to the PAV pressure control unit 18 within the PAV delivery system via 36. The electrical pulse results in a temporary decrease or increase in the output of the PAV pressure control unit relative to the output dictated by the PAV algorithm. This, then, results in either a corresponding decrease or increase in airway pressure for a brief period (for example, approximately 0.2 sec), at a time determined by the micro controller, in selected breaths.

Figure 3:
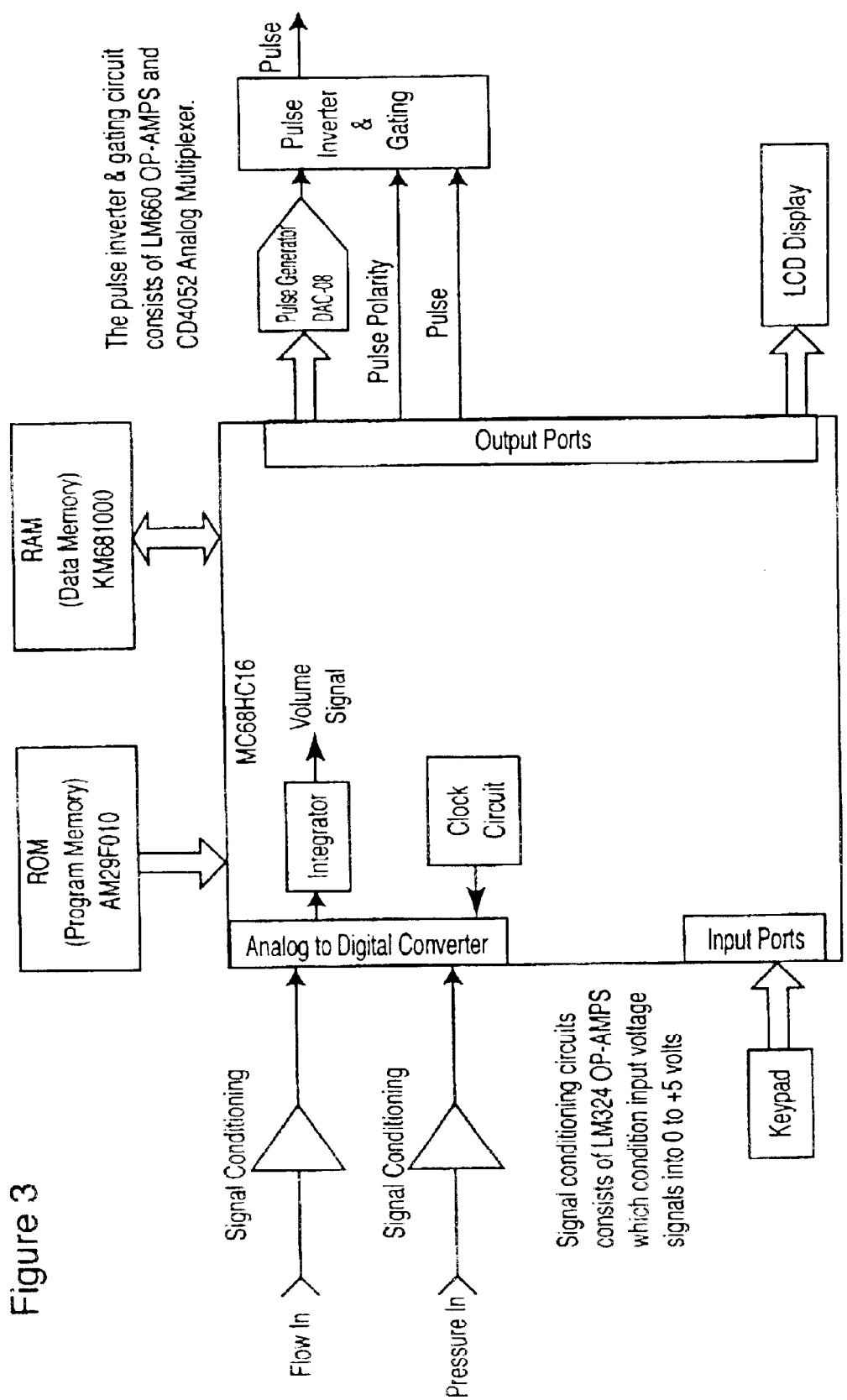
FIG. 3 shows schematically the various elements of a micro controller used in connection with the apparatus of FIG. 2.

The basic components of the micro controller 28 used in this preferred embodiment are shown in FIG. 3. The flow and airway pressure signals are passed to signal conditioning circuits ((LM324OP-AMPS) or equivalent) which condition the input voltage signals into 0 to +5 volts. The two signals are passed through to an analog to digital convertor on the micro controller. The digitized flow signal is integrated to provide inspired volume. A clock circuit allows flow, pressure and volume to be sampled at precise intervals. The basic computer is an MC68HC16 with AM29F010 ROM and KM68-1000 RAM. A preferred embodiment of the master computer program includes several functions as follows:

(1) A function to identify the beginning of inspiration. Inspiration is deemed to have started when inspiratory flow exceeds a certain threshold (e.g. 0.1 l/sec) and remains above this level for a period of at least about 150 msec beyond this point.

(2) A random number generator function generates a number between 4 and 11 which determines the number of breaths between any two successive perturbations. This results in an average of 6 unperturbed breaths between any two successive perturbations. Any other convenient integers and average may be chosen. The average number also can be over-ridden by the user through a manual input via a key pad. The user may elect to deliver the perturbations at a faster average rate to speed up the data collection or, conversely, the frequency of application of perturbations can be slowed down, as, for example, when the clinical condition is fairly stable. Clearly other methods of ensuring that pulses are applied at random intervals are possible. Pulses may also be applied at regular intervals, although this may result in anticipatory responses by the patient which may corrupt the measurements under some circumstances.

(3) An event processor function which controls the time of application and characteristics of the pulse. The timing is adjusted automatically so that the pulses are delivered in the first half of the inflation phase based on the prevailing duration of the inflation phase obtaining in previous breaths. The shape of the applied pulse is also adjusted automatically to result in a reasonably flat segment in Paw and flow during the pulse near $T_1$ (see FIG. 1). The information produced by the event processor is conveyed to the pulse generator (DAC-08, FIG. 3) which generates a pulse of about 0.2 second duration or any other convenient duration. A pulse invertor and gating circuit (LM660 OP-MPS and CD4052 analogue multiplexor, FIG. 3) is used to produce either a positive pulse or negative pulse.

(4) A subprogram that causes the values of flow, volume, and airway pressure, sampled at about 6 msec or other convenient time interval, to be stored in data memory over the entire period of inspiratory flow in breaths receiving pulses.

(5) A subprogram that scans the above data to determine the time at which peak Paw occurred prior to the negative deflection ($T_O$), a time about 100 msec or other convenient time interval prior to $T_O$ ($T_{-1}$), the time of occurrence of minimum Paw during the pulse ($T_1$) and the time of highest Paw in the post-pulse phase ($T_2$).

(6) A subprogram to tabulate values of Paw, $\dot{V}$, and volume at these four time points for each pulsed breath.

(7) A subprogram that deletes data points that fall outside the normal variability of the data. This subprogram also identifies breaths subjected to a pulse perturbation where certain criteria are not met. Data related to these observations are deleted from the tables.

(8) A program that determines the amplitude of pulses to be delivered. This is an iterative program. The pulse generator is initially instructed to deliver negative pulses of small amplitude. The decrease in flow during these pulses is noted. If the trough of the flow (i.e. $\dot{V}$ @$T_I$) is above about 0.2 l/sec or other convenient threshold value, the amplitude of the next negative pulse is increased and the trough in flow is again noted. Progressive increase in the amplitude of consecutive negative pulses continues until the trough falls at approximately 0.2 l/sec or other selected threshold value. The amplitude of the pulses is then kept constant but the trough flow is monitored each time. Should the trough rise above 0.2 l/sec or other selected threshold value and remain elevated for a number of pulses, the amplitude of the pulse is increased again. Conversely if the trough results in zero flow with resetting of respiratory cycle, the amplitude of the pulse is decreased. The intent of this subprogram is to maintain the amplitude of the negative pulses such that the trough in flow during the negative pulses is close to, but not zero.

(9) A subprogram that causes early data to be deleted as new data are acquired, leaving only the results of a specified number of pulses (e.g. last 20 pulses) in the tables.

(10) A statistical subprogram to calculate the values of respiratory system resistance (R) from equations 8, 8a, 8 inter, 8a inter, 8 (bextra) and 8a (bextra) described above. These derivations may be obtained from the average values of flow, volume and airway pressure tabulated for negative or positive pulses, as described in detail above.

(11) A function which results in the display of the results of determined resistance (R) on an LCD or other display, as required.

Whereas in the embodiment described above, a free-standing micro controller is illustrated, the same functions performed by this micro controller can be incorporated into a resident computer within the ventilator by suitable programme. It is also recognized that the application of this technology is not limited to use with the specific piston-based PAV delivery system used in the above preferred embodiment. All commercial ventilators suitable for use in the Intensive Care Unit are capable of providing outputs related to flow and airway pressure and those commercial products which have PAV delivery capabilities necessarily have circuitry or micro controllers that execute the PAV algorithm and which can be interfaced with the automated mechanics measurement system provided herein. Understandably, the system described above may have to be changed appropriately to adapt to different features in various PAV delivery system, but any such modifications required would be well within the skill of anyone experienced in the art. It is also evident that microprocessors and electronic accessories other than those described in the preferred embodiment can be utilized to accomplish the same objectives.

It is also recognized that modifications to the algorithms described above with respect to the preferred embodiment are possible. These include, but are not limited to, the following:

1) Using pulse durations that are smaller or longer than 200 milliseconds.
2) Using positive pressure pulses instead of negative pressure pulses or use of both positive and negative pulses.
3) The use of complex pulse forms, for example but not limited to, bi-phasic pulses instead of unimodel pulses.
4) More than one pulse is applied during a given breath.
5) Where transient increases or decreases in applied pressure for the sake of determining resistance are produced by transiently changing the gain of the PAV assist.
6) Where transient perturbations in pressure and flow are produced by a mechanical system independent of the ventilator itself and incorporated in the external tubing.
7) Where transient perturbations in pressure and flow, for the sake of determining resistance, are applied during modes other than PAV, including volume cycled assist, CPAP mode, pressure support ventilation or airway pressure release ventilation, whereby perturbations are produced by superimposing positive and/or negative transients to the usual control signal of the relevant mode.
8) Provision to store the resistance results over extended periods of time to be made available for later display to provide time-related trends in such relationships.

9) Provision of appropriate circuitry or digital means to effect automatic changes in the magnitude of flow assist in the PAV mode or assist level in other modes, as the resistance values change (i.e. closed loop control of assist level).

10) Where resistance is computed from values obtained from single pulses as opposed to averages of values obtained from several pulses.

11) Where the behavior of Pmus during the pulse is calculated by interpolation between values at $T_O$ and values beyond $T_1$ (as per equation 8 inter and 8a inter) as opposed to the preferred method of extrapolation of data between $T_{-1}$ and $T_O$ (as per equation 8 and 8a).

12) Where the behavior of Pmus during the pulse is calculated by backextrapolation of values occurring between $T_I$ and a point beyond $T_I$, as per equations 8 (bextra) and 8a (bextra).

13) Where resistance is calculated both by the extrapolation technique (equation 8 or 8a) and interpolation technique (equation 8 inter and 8a inter) and the result is given as an average, or derivative, of the results of the two methods of calculation.

14) Where flow is maintained nearly constant for a period of time beyond $T_1$ instead of allowing it to rise again.

15) When the assist is terminated immediately after $T_1$.

SUMMARY OF DISCLOSURE

In summary of this disclosure, the present invention provides method and apparatus to determine respiratory resistance (R) during assisted ventilation of a patent in a unique and simplified manner. Modifications are possible within the scope of the invention.

What I claim is:

1. A method of determining respiratory system resistance (R) in a patient receiving gas from a ventilatory assist device (ventilator), comprising:

estimating the flow rate ($\dot{V}$) and volume (V) of gas received by the patient from the ventilator;

estimating pressure near the airway of the patient (Paw);

generating a signal that results in a step decrease (negative pulse) in the pressure and/or flow output of the ventilator during selected inflation cycles;

measuring Paw, $\dot{V}$ and V at a point ($T_O$) near the beginning of the pulse ($Paw_O$, $\dot{V}_O$, $V_O$), at a point ($T_I$) near the trough of the negative pulse ($Paw_1$, $\dot{V}_1$, $V_1$), and at a point ($T_{-1}$) preceding $T_O$ but after the onset of inspiratory effort ($Paw_{-1}$, $\dot{V}_{-1}$, $V_{-1}$); and calculating the value of resistance (R) from the differences between Paw, $\dot{V}$ and V at $T_O$ and at $T_I$ and where the change in patient generated pressure (Pmus) in the interval $T_O \rightarrow T_I$ ($\Delta Pmus(T_O \rightarrow T_I)$) is estimated, by extrapolation, from the differences between Paw, $\dot{V}$ and V at $T_O$ and at $T_{-1}$, in accordance with equation (8), as follows:

$$R=[(Paw_O-Paw_1+(\Delta t/\Delta t_{-1})(Paw_O-Paw_{-1}))-E(V_O-V_1+(\Delta t/\Delta t_{-1})(V_O-V_{-1}))]/(\dot{V}_O-\dot{V}_1+(\Delta t/\Delta t_{-1})(\dot{V}_O-\dot{V}_{-1})) \quad (8).$$

2. The method of claim 1 wherein the estimating by extrapolation step is modified by estimating $\Delta Pmus(T_O \rightarrow T_I)$ from the differences between Paw, $\dot{V}$ and V values obtained at two time points preceding $T_O$, as opposed to $T_O$ and a single preceding time point ($T_{-1}$).

3. The method of claim 1 wherein the estimating by extrapolation step is modified by estimating $\Delta Pmus(T_O \rightarrow T_I)$ using regression coefficients obtained from regression analysis of Paw, $\dot{V}$ and V values measured at multiple (>2) points preceding the pulse.

4. The method of claim 1 wherein the estimating step to estimate $\Delta Pmus(T_O \rightarrow T_I)$ is modified by estimating by interpolation, from the differences between Paw, $\dot{V}$ and V values obtained at $T_O$ and at a second point ($T_2$) beyond $T_I$, in addition to, or instead of, extrapolation of differences between values at $T_O$ and $T_{-1}$.

5. The method of claim 1 or 3 wherein $\Delta Pmus(T_O \rightarrow T_I)$ is estimated by back extrapolation of values obtained beyond $T_I$.

6. The method of claim 1 wherein the single R value in equation (8) is replaced by mathematical functions that allow for non-linear pressure-flow relations.

7. The method of claim 6, wherein said mathematical function is given by $R=K_1+K_2\dot{V}$, wherein K1 and K2 are the coefficients defining the non-linear pressure-flow relation.

8. The method of claim 7, wherein $K_2$ is replaced by a known or assumed $K_2$ value of the endotracheal tube of the patient.

9. The method of claim 6 or 7 wherein the coefficients defining the non-linear pressure-flow relation ($K_1$, $K_2$) are obtained by regression analysis performed on the results of two or more pulses applied in separate breaths.

10. The method of claim 1, wherein a default elastance value (E) is used in lieu of an actually measured elastance value for the sake of computing differences in elastic recoil pressure between $T_O$, $T_I$ and $T_{-I}$ in equation (8).

11. The method of claim 1, wherein positive pulses are delivered instead of, or in addition to, negative pulses and the $T_I$ values of Paw, $\dot{V}$ and V are measured at or near peak Paw or flow of the positive pulse.

12. The method of claim 1, including automatically adjusting the amplitude of the pulse depending on the response to previous pulses.

13. The method of claim 1, including automatically adjusting the timing of pulse application during the inflation phase.

14. The method of claim 1, including automatically adjusting the shape of the pulse to insure the presence of a flat segment in the Paw/flow signal during the pulse for use in measuring $T_I$ values.

15. The method of claim 1, wherein the pulses are delivered at random intervals.

16. The method of claim 1 including user selecting one or more pulse characteristics.

17. The method of claim 1, wherein the resistance results (R) are reported as averages of the results of several pulses.

18. The method of claim 1, wherein resistance results (R) are stored over time to permit the display of time dependent trends.

19. The method of claim 1 including identifying pulses with results that fall outside the normal variability of the data as determined from several data sampling and excluding the results of these pulses from analysis and determination of R.

20. The method of claim 1 including deleting early data as new data are acquired and reporting the results of the determination of R for a specified number of pulses.

21. The method of claim 20 wherein the specified number of pulses is selected, either by a user or, in the absence of user input, as a default value (e.g. 20).

22. The method as claimed in claim 1, wherein the step decrease or increase in Paw or $\dot{V}$ is produced by an electromechanical system attached to the external tubing of the ventilator as opposed to directly interfacing with the ventilator control system.

23. The method of claim 1, wherein the results of the resistance values are used in closed loop control of an assist level provided by the ventilator.

24. An apparatus which interfaces with ventilatory assist devices (ventilators) and which determines respiratory system resistance (R), comprising:

a flowmeter, with associated electronic circuitry, that estimates the flow rate ($\dot{V}$) and volume (V) of gas received by a patient;

a pressure sensor that estimates pressure near the airway of the patient (Paw); and electronic circuitry which receives the Paw, $\dot{V}$ and V signals from above mentioned circuitry and which is also connected to a control system of the ventilator, comprising:

circuitry that generates an output that results in a step decrease (negative pulse) in the pressure and/or flow output of the ventilator during selected inflation cycles;

circuitry that measures Paw, $\dot{V}$ and V at a point ($T_O$) near the beginning of the pulse ($Paw_O$, $\dot{V}_O$, $V_O$), at a point ($T_I$) near the trough of the negative pulse ($Paw_1$, $\dot{V}_I$, $V_1$), and at a point ($T_{-1}$) preceding $T_O$ but after the onset of inspiratory effort ($Paw_{-1}$, $\dot{V}_{-I}$, $V_{-1}$);

circuitry to calculate the value of resistance (R) from the differences between Paw, $\dot{V}$ and V at $T_O$ and at $T_I$ and where the change in patient generated pressure (Pmus) in the interval $T_O \rightarrow T_I(\Delta Pmus(T_O \rightarrow T_I))$ is estimated, by extrapolation, from the differences between Paw, $\dot{V}$ and V at $T_O$ and at $T_{-1}$, in accordance with equation (8), as follows:

$$R=[(Paw_O-Paw_1+(\Delta t/\Delta t_{-1})(Paw_O-Paw_{-1}))-E(V_O-V_1+(\Delta t/\Delta t_{-1})(V_O-V_{-1}))]/(\dot{V}_O-\dot{V}_1+(\Delta t/\Delta t_{-1})(\dot{V}_O-\dot{V}_{-1})) \quad (8).$$

25. The apparatus of claim 24 wherein $\Delta Pmus(T_O \rightarrow T_I)$ is estimated, by extrapolation, from the differences between Paw, $\dot{V}$ and V values obtained at two time points preceding $T_O$, as opposed to $T_O$ and a single preceding time point.

26. The apparatus of claim 24 wherein $\Delta Pmus(T_O \rightarrow T_I)$ is estimated, by extrapolation, using regression coefficients obtained from regression analysis of Paw, $\dot{V}$ and V values measured at multiple (>2) points preceding the pulse.

27. The apparatus of claim 24 wherein $\Delta Pmus(T_O \rightarrow T_I)$ is estimated, by interpolation, from the differences between Paw, $\dot{V}$ and V values obtained at $T_O$ and at a second point ($T_2$) beyond $T_I$ in addition to, or instead of, as opposed to extrapolation of differences between values at $T_O$ and $T_{-1}$.

28. The apparatus of claim 24 or 26 wherein $\Delta Pmus(T_O \rightarrow T_I)$ is estimated by back entrapolation of values obtained beyond $T_I$.

29. The apparatus of claim 24 wherein the single R value in the equations is replaced by mathematical functions that allow for non-linear pressure-flow relations.

30. The apparatus of claim 29 wherein said mathematical function is given by $R=K_I+$, wherein K1 and K2 are coefficients defining the non-linear pressure-flow relation.

31. The apparatus of claim 30 wherein $K_2$ is replaced by a known or assumed $K_2$ value of the endotracheal tube of the patient.

32. The apparatus of claim 29 or 30 wherein the coefficients defining the non-linear pressure-flow relation ($K_1$, $K_2$) are obtained by regression analysis performed on the results of two or more pulses applied in separate breaths.

33. The apparatus of claim 24 wherein a default elastance value (E) is used in lieu of an actually measured elastance value for the sake of computing differences in elastic recoil pressure between $T_O$, $T_I$ and $T_{-I}$.

34. The apparatus of claim 24 wherein positive pulses are delivered instead of, or in addition to, negative pulses and the $T_I$ values of Paw, $\dot{V}$ and V are measured at or near peak Paw or flow of the positive pulse.

35. The apparatus of claim 24 including algorithms to automatically adjust the amplitude of the pulse depending on response to previous pulses.

36. The apparatus of claim 24 including algorithms which automatically adjust the timing of pulse application during the inflation phase.

37. The apparatus of claim 24 including algorithms that automatically adjust the shape of the pulse to insure the presence of a flat segment in the Paw/flow signal during the pulse for use in measuring $T_I$ values.

38. The apparatus of claim 24 wherein the pulses are delivered at random intervals.

39. The apparatus of claim 24 including a user interface that permits the user to select one or more pulse characteristics.

40. The apparatus of claim 24 wherein the resistance results are reported as averages of the results of several pulses.

41. The apparatus of claim 24 wherein resistance results are stored over minutes, hours or days to permit the display of time dependent trends.

42. The apparatus of claim 24 including algorithms which identify pulses with results that fall outside the normal variability of the data and which exclude the results of these pulses from analysis.

43. The apparatus of claim 24 including algorithms which delete early data as new data are acquired and which report the results of a specified number of pulses.

44. The apparatus of claim 43 wherein the specified number of pulses is selected by user or, in absence of user input, as a default value (e.g. 20).

45. The apparatus of claim 24 wherein some or all necessary components are incorporated within the main body of the ventilator.

46. The apparatus of claim 24 wherein the step decrease or increase in Paw or $\dot{V}$ is produced by an electromechanical system attached to the external tubing of the ventilator as opposed to directly interfacing with the ventilator control system.

47. The apparatus of claim 24 wherein the results of the resistance values are used in closed loop control of the assist level provided by the ventilator.

* * * * *